United States Patent

Gscheidmeier et al.

Patent Number: 5,826,202
Date of Patent: Oct. 20, 1998

[54] PROCESS FOR THE PREPARATION OF CAMPHENE BY THE REARRANGEMENT OF A-PINENE

[75] Inventors: Manfred Gscheidmeier, Gablingen; Harald Häberlein, deceased, late of Neusäss; Hans Harald Häberlein, heir, Neu-Ulm; Jörg Thomas Häberlein, heir, Allersberg; Mark Christian Häberlein, heir, Freiburg, all of Germany

[73] Assignee: Hoechst Aktiengesellschaft, Frankfurt, Germany

[21] Appl. No.: 758,145

[22] Filed: Nov. 25, 1996

[30] Foreign Application Priority Data

Nov. 27, 1995 [DE] Germany ........................ 195 44 086.2

[51] Int. Cl.[6] ...................................................... C07C 5/22
[52] U.S. Cl. ............................................ 585/356; 585/355
[58] Field of Search ...................................... 585/356, 355

[56] References Cited

U.S. PATENT DOCUMENTS 2,551,795  5/1951  Etzel ........................................ 585/356

FOREIGN PATENT DOCUMENTS 0539990  5/1993  European Pat. Off. .

OTHER PUBLICATIONS

*Ullmans Encyclopadie der technischen Chemie*, 3rd ed., vol. 17, Verlag Chemie, Weinheim, 1966, pp. 430–431.

Mai Lien, N., et al. *Chem. Abs. 89*: 197725g (1978).

*Primary Examiner*—Bekir Yildirim
*Attorney, Agent, or Firm*—Susan S. Jackson

[57] ABSTRACT

Process for the preparation of camphene by the rearrangement of α-pinene

A process for the preparation of camphene by the rearrangement of α-pinene in the presence of a titanium oxide hydrate catalyst under the action of heat, wherein α-pinene is refluxed until the content of α-pinene in the reaction mixture is still at least 3% by weight, and the rearrangement is then brought to completion in a secondary reaction at a temperature below 160° C.

By carrying out the process in this way—refluxing to a relatively high residual content of α-pinene and performing a secondary reaction at a lower temperature—the formation of polymeric by-products is reduced. This process moreover increases the yield of camphene in that recycled tricyclene, concentrated in the distillation of the crude product, is partially rearranged to camphene or the formation of more tricyclene is reduced.

9 Claims, No Drawings

PROCESS FOR THE PREPARATION OF CAMPHENE BY THE REARRANGEMENT OF A-PINENE

DESCRIPTION

Process for the preparation of camphene by the rearrangement of α-pinene.

The present invention relates to an improved process for the preparation of camphene, the content of isomeric tricyclene being greatly reduced compared with methods known hitherto, and the formation of high-boiling terpene polymers being very substantially avoided at the same time.

The formation of camphene by the isomerization of α-pinene under heterogeneous catalysis has been known for a long time (L. G. Gurvich, J. Russ. Phys., Chem. Soc., 47, 827/1915). A wide variety of catalysts have been proposed for this reaction, acidic titanium dioxide hydrate having proved particularly successful (summary: Ullmanns Encyclopädie der technischen Chemie (Ullmann's Encyclopedia of Chemical Technology), 3rd edition, volume 17, 1966). Above about 125° C. the reaction produces several by-products, such as tricyclene, dipentene, isomeric p-menthadienes and polymers, as well as the main product, camphene.

Cyclofenchene, α-fenchene, bornylene, Δ-3-carene, p-cymene, p-menth-3-ene and diterpenes are also formed in small amounts.

This crude camphene is worked up by fractional vacuum distillation to give technically pure camphene, which usually also contains tricyclene; in the isolated state, this cannot be utilized industrially. Tricyclene reacts chemically in substantially the same way as camphene, but can also lead to isomeric products which would interfere.

Camphene plays an important role as an intermediate, e.g. for the preparation of terpene esters (valuable and often nature-identical fragrances like isobornyl acetate, or monomers for coating resins), terpene-oxygen compounds (isoborneol, camphor), terpene ethers or alkylation products (e.g. phenols). It is frequently important here for the tricyclene content of the camphene to be below 10% if possible.

The isomerization reaction is strongly exothermic, so heat has to be dissipated. This can be done e.g. by direct cooling or circulation through a cooling apparatus in order to keep the temperature below the boiling range. This has the advantage of a small catalyst requirement (0.05–0.1% by weight) and a somewhat higher yield of camphene, while at the same time avoiding the formation of high-boiling by-products. However, the reaction then takes 10–15 times longer than a reaction carried out at the boiling point of the product. In this case, the heat of reaction is dissipated by the evaporation of α-pinene or reaction products with subsequent condensation, i.e. the reaction mixture is refluxed (C. A. vol. 89/1978, 197 725 g; EP-A-0 539 990). Under these conditions (156°–162° C., 0.2–0.4% by weight of catalyst) the isomerization proceeds rapidly in 0.75–2 hours but is less selective, especially in the final phase, mainly due to the increased formation of terpene polymers from p-menthadienes.

It has now been found that no polymers are initially formed in the isomerization of α-pinene in the presence of weakly acidic titanium dioxide hydrate as catalyst, under reflux and under a nitrogen blanket; polymer formation only occurs when the residual content of α-pinene has dropped to 5% and even more so when it has dropped to 3%. This normally happens when the boiling point rises markedly above 161.5° C. The proportion of high-boiling polymeric compounds then increases to over 5%, as a function of time, at the expense of the p-menthadienes.

This polymerization reaction can thus be avoided by lowering the reaction temperature when a particular α-pinene content has been reached, and bringing the reaction to completion at this temperature. A rapid reaction is thereby achieved by refluxing, but the formation of high-boiling polymeric products is very substantially avoided by lowering the temperature in the final phase.

The invention thus provides a process for the preparation of camphene by the rearrangement of α-pinene in the presence of a titanium oxide hydrate catalyst and under the action of heat, α-pinene initially being refluxed until the content of α-pinene in the reaction mixture is still at least 3% by weight, preferably 5% by weight, and the rearrangement then being brought to completion in a secondary reaction at a temperature below 160° C., preferably at 150°–155° C.

Specifically the process can be carried out by introducing the α-pinene and the catalyst into a stirred vessel and, under a nitrogen blanket, heating them to the reflux temperature, preferably at a rate of 0.5 to 10° C./min, preferably 2° to 4° C./min. The heat of reaction is thereby dissipated by evaporative cooling. The reflux temperature, i.e. the boiling point of α-pinene or of the reaction mixture formed during the rearrangement, depends on the purity of the α-pinene. The reflux temperature is generally about 155° to 165° C. The reaction time is 0.3 to 3.5 h, preferably 0.7 to 1.5 h, depending on the catalyst concentration and the heating rate.

The catalyst is conventional titanium oxide hydrate or, preferably, a titanium oxide hydrate obtained by the following procedure: A $TiO_2$ paste acidified with sulfuric acid is treated with NaOH solution, washed, stirred with acetic acid, filtered off with suction and then dried under vacuum at 50° to 100° C., preferably at 60° to 80° C.

The amount of catalyst to be used is 0.1 to 2.0% by weight, preferably 0.3 to 0.5% by weight, based on pure α-pinene.

When the reflux temperature has been reached, the reaction mixture is kept at this temperature until the content of α-pinene in the reaction mixture has dropped to about 3% by weight, preferably to about 5% by weight. The decrease in the content of α-pinene during the rearrangement reaction can easily be monitored by suitable analytical methods, for example by gas chromatography. When these residual amounts of α-pinene are attained in the reaction mixture, the internal temperature of the reaction mixture is lowered and the conversion of the α-pinene still present is brought to completion in a secondary reaction at lower temperatures. The temperature in this secondary reaction depends on the boiling point of the reaction mixture. It is expedient to lower the temperature in the secondary reaction to about 10° C. below the boiling point of the reaction mixture. This generally means a temperature of about 150°–155° C. The temperature should at any event be below 160° C. The duration of the secondary reaction depends on the particular residual content of α-pinene desired. When the desired residual amount, for example 0.1% by weight of α-pinene, has been reached, the reaction mixture is cooled, the catalyst is filtered off and the camphene is separated from the by-products by distillation.

One variant of the process according to the invention uses a less active titanium oxide hydrate catalyst or a smaller amount of a more active catalyst of this type. Although the main reaction then requires somewhat more time, the reaction temperature in this case automatically falls below the boiling point toward the end of the α-pinene isomerization, so active cooling is no longer necessary for the secondary reaction.

The isomerization of α-pinene always produces tricyclene in addition to camphene, the proportion of tricyclene depending on the reaction temperature. At a reaction temperature of 155° C., for example, 13.6% by weight of tricyclene is obtained in the reaction mixture or 17.1% by weight is obtained in the fraction from which p-menthadiene has been removed. It has now been found that this equilibrium value is also obtained when a product mixture with a high tricyclene content is subjected to the same isomerization conditions as α-pinene. The equilibrium value in this case is reached considerably more rapidly than in the isomerization of a mixture with a correspondingly lower tricyclene content. As tricyclene is highly concentrated (up to more than 50%) in a first distillation cut in the distillative working-up of the α-pinene isomerization product under vacuum, because of the somewhat higher vapor pressure of said tricyclene, it is now possible to separate off this tricyclene-enriched first distillation cut and recycle it into an isomerization batch with α-pinene. The equilibrium ratio is then reached again at the appropriate boiling point, meaning either that a tricyclene content in excess of the equilibrium value prevailing at the boiling point is converted to camphene, or that, if the tricyclene content is below said value, more tricyclene is formed only until the equilibrium value is reached. In the case of tricyclene-enriched fractions, it is therefore possible for tricyclene to be converted to camphene. It is of course also possible to subject only the tricyclene-rich distillation cut to the same isomerization conditions as α-pinene. It is advantageous that no p-menthadienes, and hence no high-boiling by-products, are produced here. As a consequence of separating off a tricyclene-rich first cut from the crude camphene distillation, a main camphene fraction is obtained which now contains on average substantially less tricyclene, down to well below 10%, depending on the tricyclene content and the quantity of the first cut.

The process according to the invention thus makes it possible to reduce the proportion of polymeric by-products in the conversion of α-pinene to camphene and hence to increase the proportion of camphene. It is moreover possible to reduce the proportion of tricyclene in the camphene by separating off a first tricyclene-rich fraction in the distillative working-up of the reaction mixture and recycling this enriched fraction into the isomerization reaction.

EXAMPLE 1 (Comparative Experiment)

Isomerization of pinene without the addition of tricyclene first runnings; temperature rises above 162° C.:

In a 5 m³ jacketed vessel equipped with a stirrer, 3038 kg of technical-grade α-pinene about 96% of α-pinene, ca. 1.5% of β-pinene about 1% of camphene) and 12 kg of weakly acidic titanium dioxide hydrate were heated to 155° C. under a constant nitrogen blanket, with stirring. As a result of the exothermic isomerization reaction, the temperature of the reaction mixture rose to the boiling point of the α-pinene or the isomerization products. The product vapors were condensed and the condensate was recycled into the reactor without further cooling. When the α-pinene content had dropped to 0.1%, after about 60 min, the reaction was ended by cooling, at which point the internal temperature was 163.1° C. with a slight tendency to increase. After filtration of the reaction mixture, analysis showed 7.2% of high-boiling polymeric products, formed exclusively via p-menthadienes, and tricyclene (T), camphene (C) and p-menthadienes (p-M) (mainly α-terpinene, y-terpinene, dipentene, terpinolene) in the weight ratio T:C:p–M= 1:4.3:0.9.

EXAMPLE 2

Isomerization of pinene without the addition of tricyclene first runnings

Analogously to Example 1, 2994 kg of α-pinene and 7.5 kg of weakly acidic titanium dioxide hydrate were reacted at the boiling point. The reaction temperature rose to about 162° C. in this process and then began to fall slightly. The reaction mixture was cooled after about 80 min. It contained only 0.1% by weight of high-boiling polymeric products; the weight ratio tricyclene:camphene:p-menthadiene was 1:4.8:1.8.

EXAMPLE 3

Isomerization of pinene with the addition of tricyclene first runnings

Analogously to Example 1, 3000 kg of α-pinene and 350 kg of tricyclene first runnings (containing 49% of tricyclene) were reacted with 7.5 kg of weakly acidic titanium dioxide hydrate. The reaction temperature rose to 161.2° C. and then began to fall slightly. The reaction was stopped by cooling after about 120 min. The reaction mixture contained only 0.2% by weight of high-boiling polymeric components; the weight ratio tricyclene:camphene:p-menthadiene was 1:4.5:1.3.

EXAMPLE 4

Isomerization of pinene with the addition of tricyclene first runnings

Analogously to Example 1, 3022 kg of α-pinene and 309 kg of tricyclene first runnings (containing 51% of tricyclene) were reacted with 10 kg of weakly acidic titanium dioxide hydrate. After the reaction temperature had risen to 161.7° C. and the α-pinene content had dropped below about 3%, the reaction mixture was cooled to 150° C. and stirring was continued for ca. 1 hour at this temperature. When the reaction was complete, i.e. when the residual content of α-pinene was below 0.1% by weight, the reaction mixture was cooled. It was completely free of high-boiling polymeric by-products; the weight ratio tricyclene:camphene:p-menthadiene was 1:4.6:1.5.

We claim:

1. A two-step process to reduce the proportion of polymeric by-products in the conversion of α-pinene to camphene and to increase the proportion of camphene comprising:
   reacting α-pinene in the presence of a titanium oxide hydrate catalyst in a reaction mixture at a temperature of 155° C. to 165° C.;
   monitoring the content of said α-pinene in said reaction mixture until said α-pinene amount has dropped to about 3% by weight and carrying out the remainder of said reaction at a temperature below 160° C. and below first reacting temperature.

2. The process as claimed in claim 1, wherein said α-pinene is refluxed until the content of said α-pinene in said reaction mixture is still at least 5% by weight.

3. The process as claimed in claim 1, wherein said remainder of said reaction is brought to completion at a temperature of 150° C. to 155° C.

4. The process as claimed in claim 1, wherein said remainder of said reaction is brought below 160° C. by cooling of said reaction mixture.

5. The process as claimed in claim 1, wherein said reaction mixture is worked up by distillation, and a tricyclene-enriched fraction obtained from said distillation is recycled by combining it with said α-pinene to be reacted with said titanium oxide hydrate catalyst.

6. A process for the preparation of camphene by the rearrangement of α-pinene, as the starting material, in a reaction mixture containing an acidic catalyst under the action of heat, comprising:

carrying out the rearrangement in a plurality of heating steps, a higher-temperature heating step and a lower-temperature heating step; said higher-temperature heating step being carried out with refluxing of the α-pinene starting material until the content of α-pinene in the reaction mixture is still greater than 3% by weight, then completing the rearrangement in the lower-temperature heating step, the temperature of said lower-temperature heating step being below 160° C.

7. The process as claimed in claim 6, wherein the acidic catalyst comprises a titanium oxide hydrate.

8. The process as claimed in claim 6, wherein the said higher-temperature heating step is carried out until the content of α-pinene in the reaction mixture is still at least 5% by weight, and the lower-temperature heating step is begun when essentially no polymeric compounds with a boiling point above that of α-pinene are present in the reaction mixture.

9. The process as claimed in claim 8, wherein said lower-temperature heating step is carried out at a temperature not exceeding 155° C.

* * * * *